United States Patent [19]

Curlee

[11] Patent Number: 4,622,957

[45] Date of Patent: Nov. 18, 1986

[54] THERAPEUTIC CORSET

[76] Inventor: James D. Curlee, 1115 Lisburn Rd., R.D. 3, Mechanicsburg, Pa. 17055

[21] Appl. No.: 627,462

[22] Filed: Jul. 3, 1984

[51] Int. Cl.$^4$ .......................... A61F 5/03; A61F 5/34
[52] U.S. Cl. ...................................... 128/78; 128/118
[58] Field of Search ................................ 128/78, 118

[56] References Cited

U.S. PATENT DOCUMENTS

| | | | |
|---|---|---|---|
| 1,646,590 | 4/1926 | Mildenberg | 128/78 |
| 2,554,337 | 10/1946 | Lampert | 128/78 |
| 3,071,133 | 12/1960 | Eisen | 128/78 |
| 3,521,623 | 2/1965 | Nichols et al. | 128/78 |
| 4,135,503 | 1/1979 | Romano | 128/78 |
| 4,175,548 | 11/1979 | Henry | 128/78 |
| 4,178,922 | 12/1979 | Curlee | 128/78 |

FOREIGN PATENT DOCUMENTS 2454702 11/1974 Fed. Rep. of Germany ........ 128/78
1461408 6/1965 France ..................... 128/78

Primary Examiner—Edgar S. Burr
Assistant Examiner—Tonya Eckstine
Attorney, Agent, or Firm—John S. Roberts, Jr.

[57] ABSTRACT

An improved therapeutic corset which is peculiarly adapted for the sacrum, lumbar and thoracic region of the body comprises an elongated support surface formed from material that is bendable when subjected to forces encountered thereby. Disposed on the support surface and secured thereto along its edges is a flexible cover disposed thereover to form an envelope. The envelope is provided with a duct of introducing fluid therein and retaining same, thus inflating the envelope causing the surface to bend to assume a predetermined curvature, which is preferably in the shape of a crescent. The support surface is further equipped with a fastener removably securing the free ends of same to the wearer.

13 Claims, 9 Drawing Figures

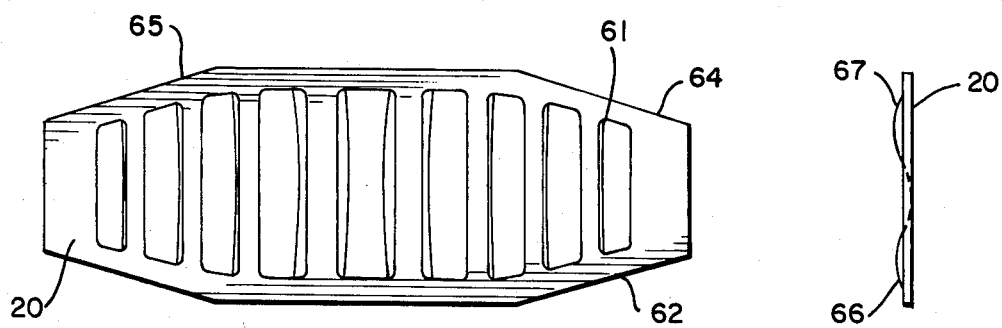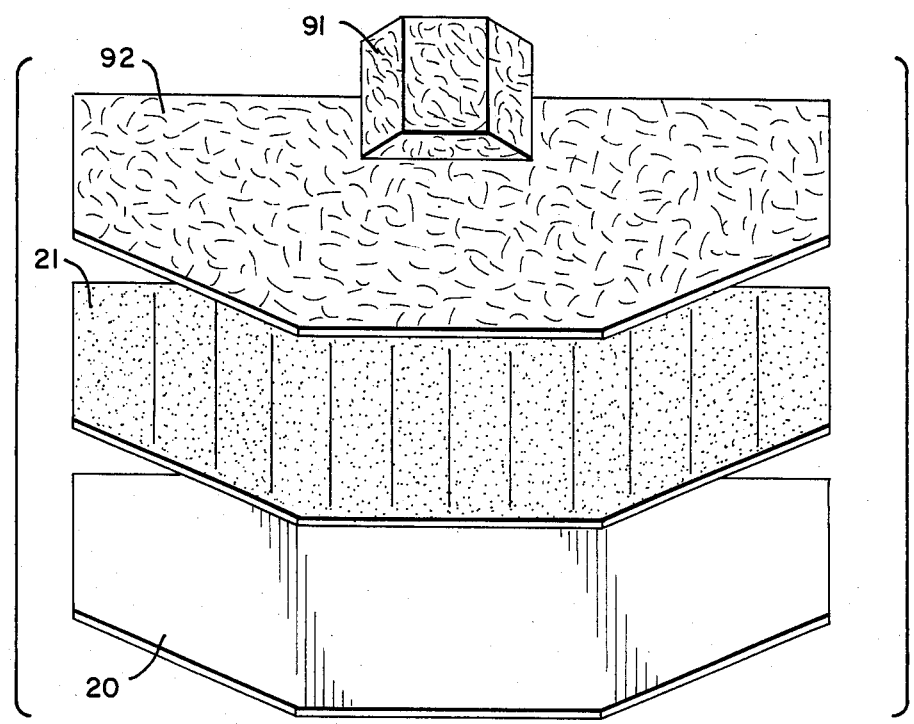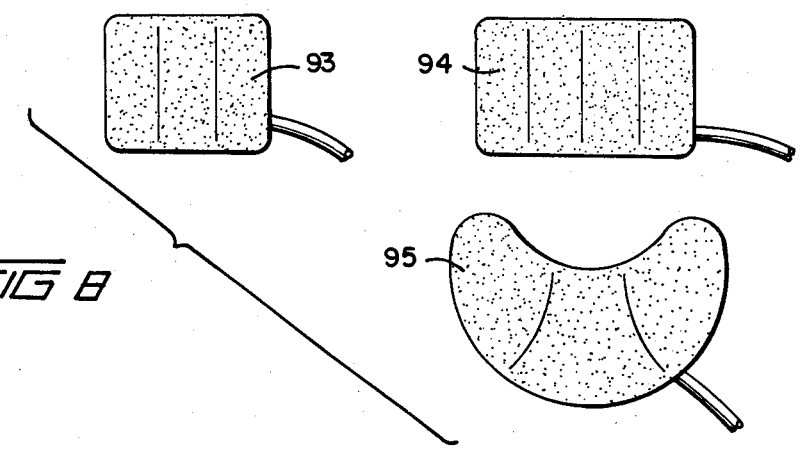

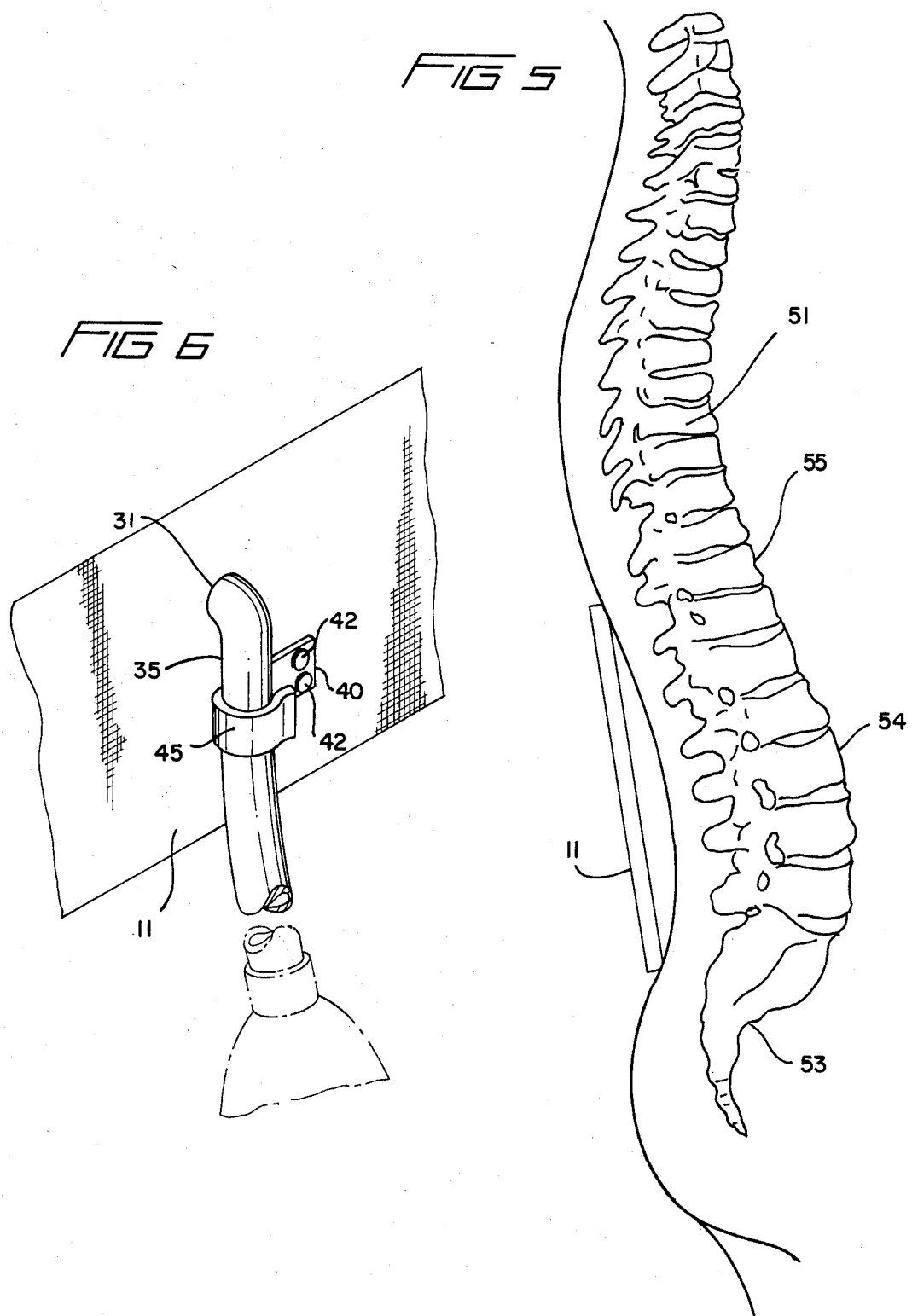

THERAPEUTIC CORSET

FIELD OF THE INVENTION

The present invention relates generally to therapeutic devices and more particularly to a corset appliance which may be applied to that region of the human body comprised of the sacro-lumbar and thoracic areas in order to prevent or treat injuries to the aforenoted region.

BACKGROUND OF THE INVENTION

As is well known, the human spine or spinal column is comprised of seven cervical vertebrae, twelve thoracic vertebrae, and five lumbar vertebrae. The vertebrae are disposed in a stacked array and interposed between the same are fibrocartilages or discs. Thirty one pairs of spinal nerves are also associated with the spinal column and the nerves are sometimes adversely affected by means of the relative disposition of one or more vertebrae whereby severe pain results. For example, when the back area sustains a contusion or is subjected to uneven stress or the like, a displacement or misalignment of one or more of the vertebrae can occur which is capable of causing pressure to be exerted on the spinal nerve roots.

In light of the above, it is commonly recognized that where a particular misaligned vertebrae is re-aligned in conjunction with the residual, properly aligned vertebrae, the pressure upon the spinal nerves is alleviated with a consequent lessening of pain suffered by the patient. Such re-alignment of the misaligned vertebrae is normally accomplished as a result of pressure being applied to the afflicted areas of the body by means of direct application of pressure to the afflicted area. In accordance with these principles, prior art therapeutic appliances have been developed in order to attempt to provide such counter-pressure to the affected body regions.

Prior art appliances of the aforenoted type are exemplified by those disclosed in French Pat. No. 1,461,408 issued to M. Gross, U.S. Pat. No. 4,135,503 to N. A. Romano, and U.S. Pat. No. 4,178,923 issued to J. D. Curlee. The appliances include an inflatable bladder which seeks to exert the aforementioned counterpressure upon the afflicted body portions as a result of the inflated expansion thereof. It has been found, however, that devices such as those exemplified by U.S. Pat. No. 1,461,408 to Gross, while providing a generalized support to the afflicted region generally, are not capable of exerting the desired counter-pressure at the precise body location as required. This characteristic can be seen in those therapeutic corset appliances which, when applied to an area of the back encompassing the sacro-lumbar and thoracic regions, is incapable of providing adequate contact and necessary directed counterpressure to specific areas such as the peculiar spinal curvature of the sacro-lumbar region. Further, when such prior art appliances are normally employed, adequate contact and pressurization of the afflicted body region is usually accomplished by means of increased tightening of the appliance about the patient's midsection (torso) or increasing the degree of pressurization of the bladder generally. These methods can be dangerous in that other portions of the body may thereby be deleteriously affected. This is particularly true where increased tightening of the appliance is utilized as a means of affecting increased pressurization of the afflicted body region, since such tightening serves to dangerously constrict the cardiovascular network of the body and generally provides increased discomfort to the wearer.

Another disadvantage has presented itself as a result of elastic properties of many prior art bladder devices, wherein bladders have a high coefficient of elasticity. As the pressure therein is increased, the contact area defined between the bladder and the body is increased and the cardiovascular network of the body is severely constricted in a manner similar to that accomplished by means of a conventional blood pressure cuff. Prolonged usage of such appliances can result in major complications, such as, for example, renal isclemia, muscle spasms, or arteriosclerosis-related problems. Where prior art appliances, such as Curlee and Romano, supra, have utilized individual air cell pockets of material exhibiting a low coefficient of stretchability, adequate contact and counterpressure at precise body locations has been accomplished and maintained without threat of constricting the body's cardiovascular network, but at the expense of failing to provide a more generalized and effective support to the muscle structure of the back area related to the lumbar thoracic region of the spinal column.

It has also been found that prior art therapeutic devices, such as that shown in Curlee above, while exerting the desired counterpressure at precise body locations, do not and cannot, in fact, provide an effective and comfortable support to the entire muscle mass related to the lumbar and thoracic regions of the lower back. This is particularly characteristic of corset appliances which, when applied to the lumbar/thoracic regions of the human back in instances requiring the application of specific counterpressure to precise spinal locations. In such circumstances, utilizing means such as an inflated bladder device, such prior art appliances have been unable to provide simultaneous, deliberate and comfortable counterpressure supportive to the general muscle mass connected with the lumbar/thoracic region.

In light of the above, the present invention will provide a new and improved therapeutic corset appliance which will overcome the various disadvantages of prior art appliances and provide a device which is adapted to be applied to the sacro-lumbar/thoracic area of the body. Said device of the present invention is adapted to be applied to the lumbar/thoracic area of the human back and is capable of applying precisely localized counterpressure to specifically afflicted areas of the aforesaid back region and will accommodate the unique curvature of the sacro-lumbar area of the aforenoted region. Such accommodation, as well as the needed localized counterpressure, may be provided in the context of a broader support to the general muscle mass connected with the sacro-lumbar and thoracic region of the human back.

Such advantages will be gained by the present invention's use, in its preferred embodiment of a plurality of vertically spaced inflatable air cells mounted on a rigid or semirigid backing wherein padding can be applied at various positions to fill contours of the back to insure total contact with the aforementioned region, and/or to provide an adjustable means of regulating the application of precise localized counterpressure to afflicted areas as desired. Such objects are further enhanced by means of a tapered support which will avoid interference with the wearer's hip region or ribcage and provide maximum comfort and increased sacro, lumbar and thoracic region support.

SUMMARY OF THE INVENTION

The foregoing and other objectives of the present invention are achieved through provision of a therapeutic corset appliance which consists of an elongated rigid or semi-rigid support surface vertically disposed to encompass the sacrum, lumbar, and thoracic areas of the human back. Said support surface is formed from material that is bendable when subjected to forces encountered thereby. Disposed on said support surface is a flexible bladder possessing a low coefficient of stretchability which is secured thereto along its edges and may also be secured along a horizontal line bisecting the support surface nearest the wearer at a point equidistant to its edges.

The bladder of the corset is further divided into at least two intercommunicating cells that are formed by dividing the bladder along certain lines by stitching or other suitable means. A means of retaining fluid and a means of introducing fluid into said bladder is utilized for inflating same. While inflated, a means will cause said support surface to bend to assume a predetermined curvature or crescent of no less than 30°. Disposed upon said support surface are means removably securing said support to a corset belting material which in turn is provided with means removably securing same to the wearer. The preferred arrangement of the support will contain a bladder laterally divided along the axis of the corset. Said bladder will contain multiple ribs in a nesting parallel configuration perpendicular to the axis of the corset. The bladder is preferably stitched to form the cells. Additional padding may be applied to the corset and secured to the support surface on the side next to the user to cushion, fill, and provide additional directed counterpressure to specific areas of the back. Padding may also be disposed wrapped around the the top of the belting material and the bladder and backing may be contoured and narrowed in width along its ends to avoid the hip and ribcage of the user.

DESCRIPTION OF THE FIGURES

Various additional objects, features, and advantages of the invention will be better understood from the following description when considered in conjunction with the accompanying Figures, to wit:

FIG. 4 is a perspective view of the corset support backing.

FIG. 5 is a schematic view showing the application of the corset structure to the sacro, lumbar, and thoracic region of the human body.

FIG. 6 is a perspective view of the air pump attachment means.

FIG. 7 is an expanded view of the corset and inflatable unit with additional padding means.

FIG. 8 is a perspective view of additional embodyments of optional inflatable padding means.

SPECIFIC DISCLOSURES

Figure 1:
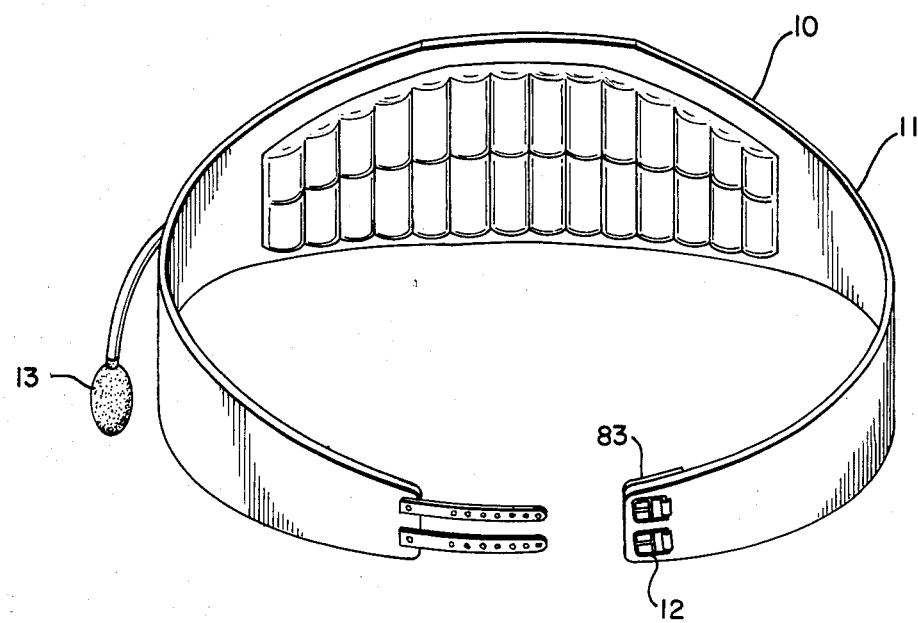
FIG. 1 is a perspective view of the improved therapeutic corset appliance onto which an inflatable unit is attached.

Referring to the drawings and more particularly FIG. 1 thereof, the improved therapeutic corset is generally indicated by character 10. The corset is comprised of a flexible belting material 11 which is capable of wrapping around the waist of the user. The belting material is further equipped with a fastening means for removably securing same to the wearer, such as a buckle device 12 or any other suitable mechanism. Suitable padding 83 may be disposed upon the buckle device 12 to provide additional comfort. The width of said belt 11, as can readily be seen in FIG. 5, will be sufficient, when applied to the spinal area 51, to encompass the sacrum 53, lumbar 54, and thoracic 55 regions of the spinal column. An inflation device such as an air pump 13 (FIG. 1) can be attached to the outside of the corset 10 by any means capable of holding it in position. The preferred method of attaching said inflation device is by means of a "C" ring clip holder consisting of a spring clasp made of suitable plastic, steel or other suitable material.

FIG. 6 shows the air pump attachment means 40, which can be secured to the belting material 11, by rivets 42, or other suitable fastening means. The air pump attachment means 40, is disposed on the belting material 11, directly below the access hole 31, through which the tube 35 from the air bladder 21 extends. The air pump attachment consists of a "C" ring or spring clasp 45, which can be constructed from any suitable material having elastic properties such as plastic or stainless steel.

Figure 2:
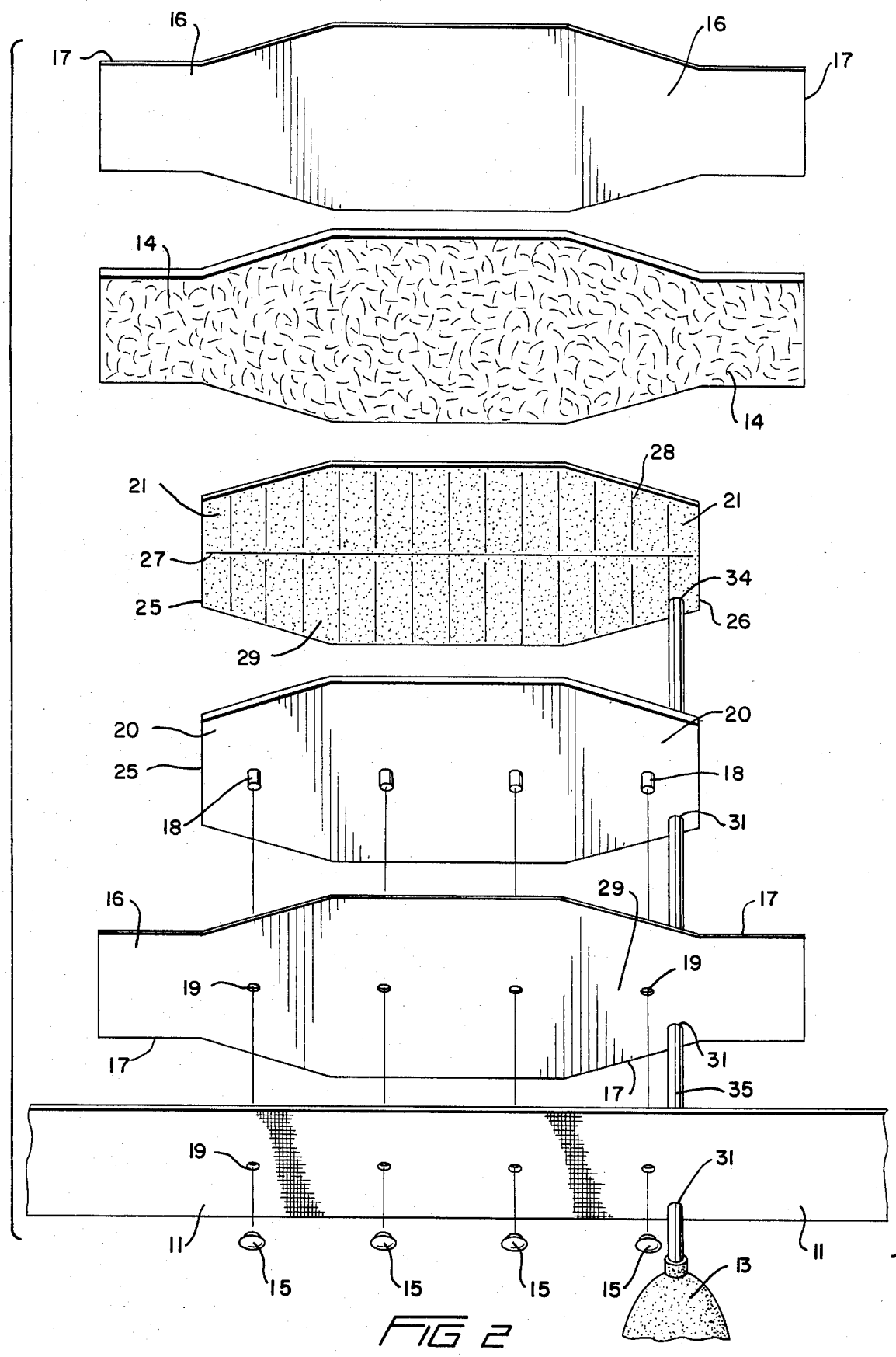
FIG. 2 is an expanded view of the inflatable unit showing its disposition in relation to other components of the therapeutic corset appliance.

With reference to FIG. 2, the therapeutic corset consists of a support surface 20, which can be formed from material that is bendable when subjected to forces encountered thereby. A flexible bladder 21 consisting of material possessing a low coefficient of stretchability is disposed on said support surface 20, secured or bonded by any suitable means along its edges 25, 26. The bladder 21 can also be secured at a point along the horizontal axis of the corset device 27, thereby forming at least two intercommunicating cells 28, 29 in a parallel configuration, disposed along the latitudinal axis of the corset. Said bladder 21 will thereby form an inflatable support surface of a substantially rectangular configuration, although said surface may also be disposed in an elliptical configuration. Fluid may be introduced into the bladder 21 by means of a circular cavity 34 or other suitable means to which a tube 35 or the like is attached and secured so as to effect a seal and provide a duct through which fluid can be transferred into the bladder from an air pump or other suitable device 13.

Disposed against the bladder 21 on the side closest to the wearer, is a padding means 14, which may be constructed of any suitable material. Liner material 16 is disposed so as to surround the bladder 21, support surface 20, and padding 14, and may be sewn or otherwise bonded around its entire perimeter 17. Fastening studs 18 may be disposed on the side of the support surface away from the wearer. Such studs 18, may protrude through holes 19 in the liner 16 and the belting material 11. Said studs line up with holes in the belting material 19 and attach securely by means of rivet heads 15 or other suitable means. In addition, the support surface 20, liner 16, and belting material 11 contain access holes 31 through which the air tube 35 extends from the bladder 21, and to which the air pump 13 is attached.

Figure 3A:
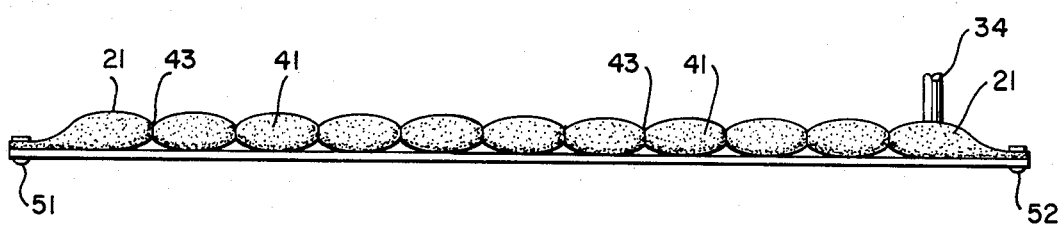
FIG. 3a is a perspective view of the inflatable unit.

The construction and application of the bladder itself can best be understood in light of FIGS. 3a and b, wherein FIG. 3a shows an embodiment of the bladder 21 with means 34 of introducing fluid therein. The bladder 21, can be made of any type of material possessing a low coefficient of elasticity capable, when formed into a bladder, of holding compressed air or other fluid under pressure. Said bladder 21, in its preferred embodiment, will be divided into at least two intercommunicating cells 41 nesting in a parallel configuration perpendicular to the axis of the corset (FIG. 1). Said cells can be formed by stitching or other suitable means to form ribs 43 which will permit the passage af fluid from one cell to another to affect inflation. Stitching may also be utilized along the longtitudinal axis of the corset to further divide the bladder.

Figure 3B:
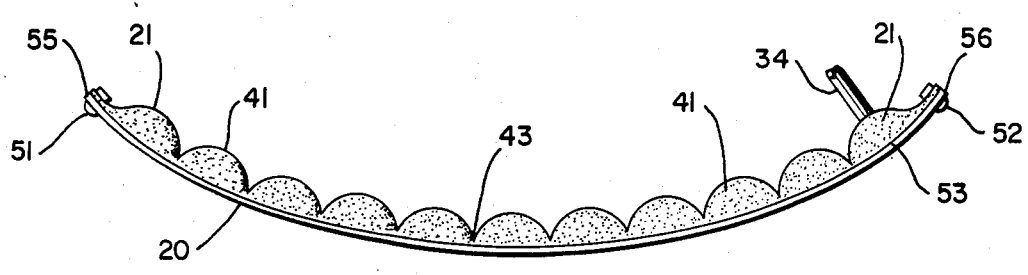
FIG. 3b is a perspective view of the inflatable unit mounted on its support backing.

The corset is constructed, as can be readily observed in FIG. 3b, by attaching the bladder 21 to a rigid or semirigid support surface 20 at its ends 51,52, around its perimeter 53, or overall with adhesive. When the envelope is inflated, as can be seen in FIG. 3b, such attachment acts to pull the extremeties of the support surface 55,56 into a crescent shape in excess of 30° corresponding to the natural shape of the human body at the sacro, lumbar and thoracic region of the torso.

Left unattached to its rigid or semirigid backing or support surface 20, the entire bladder 21 of cells 41 would shrink in length during inflation. Thus, the support surface 20, controls the amount of shrinkage, which is important in maintaining where each individual cell 41 will apply counterpressure. Thus, the method of attachment of the envelope to the backing will dictate the degree of shrinkage and the ultimate shape of the support 20 at full inflation.

Also, by chosing the exact method of attachment of the bladder 21 to the support surface 20, the amount of fluid volume of the cells 41 can be controlled. This reduces bulk while maintaining the pressure equivalent of a non-attached bladder. When the bladder is divided 43 to form such cellular configuration, each cell 41 balloons to form a pressure pad of certain size and configuration.

The preferred construction of the support surface 20 can itself be seen in FIG. 4, wherein it can be seen that the support 20 may be of flat rigid or semirigid construction and may consist of two independent but intercommunicating sections 61, 62 which, while of substantially rectangular configuration, can be tapered 64, 65 at its extremities so as to accomodate the wearer's hips and ribcage. The construction of the support surface itself, may be such as to incorporate a longitudinal reinforcement 66 in the shape of an arc 67, the apex of which would face the inside of the corset and extend outward on the side of the corset away from the wearer. Such construction would allow the surface 20 to remain rigid against bending in a vertical plane and yet allow it to remain flexible and able to bend horizontally into a crescent shape.

FIG. 7 reveals the disposition of additional padding 91, 92 which can be applied to the corset and secured to the support surface 20 and bladder 21 on the side next to the user, for the purpose of "filling" the unique contours of the sacro-lumbar region of the spine, or for providing more precise counterpressure or comfort to specific areas while controlling the overall stability of the sacrum-thoracic spinal region. In the embodiment shown in FIG. 7, a trapezoidal pad can be applied to the corset at any point for the purpose of filling the contours of the back, thus assuring total contact. At FIG. 8, other embodiments of various additional padding and support means 93, 94 and 95, which are constructed in a manner similar to the bladder, and which are capable of being inflated separately, or along with the bladder. Said additional padding and support means are capable of being incorporated onto the support surface and preferred bladder by utilizing a liner or other suitable means. The use and flexible disposition of said additional padding and support means serve to permit a flexible application of precise supportive counterpressure at various locations and pressures as required.

What is new and desired to be secured by Letters Patent is:

1. A therapeutic corset-type appliance to be worn by a person about the torso of the human body to effectively treat the sacrum, lumbar, and thoracic regions of the person's back, comprising:
   (a) belt means, having inside and outside surfaces, for securing said therapeutic appliance about said torso portion of said person's body;
   (b) means for mechanically releasing spasm muscle tissue and applying pressurized forces to the sacrum, lumbar, and thoracic regions including a semi-rigid support surface and an inflatable bladder means;
   (c) said support surface having inside and outside surfaces, said outside surface of said support surface being secured to said inside surface of said belt means, said support surface having a vertical height extending from and between said sacrum, lumbar and thoracic regions and having an around-the-body width encompassing the sacrum, lumbar and thoracic regions;
   (d) said inflatable bladder means having inside and outside surfaces, said outside surface of said bladder means being secured to said inside surface of said support surface so that said cells are nested within said support surface when said belt means is attached to the person's body, said inflatable bladder means being comprised of material possessing a low coefficient of elasticity relative to the bendability of the semi-rigid support surface and being divided into a series of laterally spaced, vertically extending, separate and distinct, yet fluidically interconnected, inflatable cells;
   (e) means for causing said belt means and said support surface to bow in an arcuate manner about a vertical axis parallel to the height axis of said person's body upon inflation of said cells, said means for causing consisting of the low coefficient of elasticity of said bladder means compared to the bendability of said support surface and said nesting of said cells;
   (f) means secured to said belt means, and fluidically connected to said inflatable bladder means, for inflating said inflatable bladder means.

2. The therapeutic corset of claim 1, wherein the cells are formed by stitching inflatable bladder material along predetermined lines.

3. The therapeutic corset appliance as set forth in claim 1, further comprising:
   padding means covering said inflatable bladder means; and
   liner means covering said padding means.

4. The therapeutic corset of claim 3, wherein the support surface, padding means and inflatable bladder means are enveloped in said means so as to form a modular unit.

5. The therapeutic corset of claim 3, wherein the support surface contains fastening studs which protrude through holes on one side of said liner means.

6. The therapeutic corset of claim 1, wherein said belt means contains holes through which fastening studs may protrude.

7. The therapeutic corset of claim 1, wherein additional padding is secured to said inflatable bladder means on the side next to the user thereof.

8. The therapeutic corset of claim 1, wherein the inflatable bladder means is contoured and narrowed in width along its ends to avoid the hip area and ribcage of the user.

9. The therapeutic corset of claim 1, wherein:
said support surface is removably secured to said belt means by removable means; and
fastening means are disposed at the ends of said belt means with padding means disposed thereon.

10. The therapeutic corset of claim 3, wherein the support surface, liner means and belt means, contain at least one access hole.

11. The therapeutic corset of claim 10, wherein a clasp is attached to the belt means at a point below the access hole.

12. The therapeutic corset of claim 11, wherein said clasp is formed in the shape of a crescent for frictionally securing an object therein.

13. The therapeutic corset of claim 1, wherein cushioning elements are attached to the inflatable bladder means on the side opposite the support surface.

* * * * *